US00PP33205P2

(12) United States Plant Patent
Ranney et al.

(10) Patent No.: US PP33,205 P2
(45) Date of Patent: Jun. 29, 2021

(54) AZALEA PLANT NAMED 'NCRX4'

(50) Latin Name: ***Rhododendron* hybrid**
Varietal Denomination: NCRX4

(71) Applicant: North Carolina State University, Raleigh, NC (US)

(72) Inventors: Thomas Green Ranney, Arden, NC (US); Darren H. Touchell, Raleigh, NC (US); Irene Palmer, Raleigh, NC (US); Andra Windorf Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/902,774

(22) Filed: Jun. 16, 2020

(51) Int. Cl.
*A01H 5/00* (2018.01)
*A01H 6/36* (2018.01)

(52) U.S. Cl.
USPC ..... Plt./240

(58) Field of Classification Search
USPC ..... Plt./238, 239, 240
See application file for complete search history.

(56) References Cited

PUBLICATIONS https://springmeadownursery.com/plantfinder/perfecto-mundo-purple. Retrieved from internet on Nov. 16, 2020, (2 pages total).*
youtube-azaleaperfecetomundodoublepurple.pdf. Retrieved from the internet on Nov. 16, 2020, (1 page total).*

* cited by examiner

*Primary Examiner* — Susan McCormick Ewoldt
(74) *Attorney, Agent, or Firm* — Cassandra Bright

(57) ABSTRACT

A new and distinct cultivar of *Rhododendron* plant named 'NCRX4' having large, semi-double lavender flowers, a profuse spring flower display, fall reblooming, and a dense, compact habit. Plants exhibit mid-sized habit and propagate readily from stem cuttings. The new cultivar is a *Rhododendron*, suitable for ornamental garden purposes.

3 Drawing Sheets

Latin name of the genus and species: The Latin name of the novel plant variety disclosed herein is *Rhododendron* hybrid.

Variety denomination: 'NCRX4'.

BACKGROUND OF THE INVENTION

The inventive hybrid was selected from seedlings derived from an open-pollinated experimental hybrid azalea (unpatented) with the experiental code H2009-237-023 and was given the varietal denomination of 'NCRX4'.

The present invention comprises a new and distinct hybrid evergreen azalea cultivar hereinafter referred to by the cultivar name 'NCRX4'. This hybrid azalea was selected for its large semi-double lavender flowers, moderate and dense growth habit, and strong reblooming behaviors. 'NCRX4' was obtained from the open-pollination of the female experimental hybrid H2009-237-023. 'NCRX4' was selected after 8 years in trials at a research nursery in Mills River, N.C. Trials were conducted in full sun with bark-amended clay soils with minimum winter temperatures of −2° F. (−19° C.) and maximum summer temperatures 98° F. (37° C.). The first asexual propagation of 'NCRX4' occurred in 2011 by rooting stem cuttings at the research nursery in Mills River, N.C. 'NCRX4' roots readily from firm softwood cuttings treated with a basal dip of 3000 ppm indole butyric acid (potassium salt) in water. 'NCRX4' has been found to retain its distinctive characteristics through successive asexual propagations over the course of 8 years.

SUMMARY OF THE INVENTION

The following are the unique combination of characteristics of this new cultivar when grown under standard horticultural practices at North Carolina State University, Mountain Horticultural Crops Research Station, Mills River, N.C.

1. Profuse spring flower display.
2. Large, semi-double, lavender flowers.
3. Cold hardiness to at least 0° F., USDA Zone 6B
4. Dense, habit, mid-size plant.
5. Reblooming in the summer and fall.

COMPARISON TO PARENT VARIETIES

Records of the parent variety characteristics are not available. The inventor cannot make a comparison to the seed parent. The pollen parent is unknown.

COMPARISON WITH COMMERCIAL CONTROLS

TABLE 1

| Plant | Flower Color and Type |
|---|---|
| Hybrid azalea 'Roblez' U.S. Plant Pat. No. 28,279 P3 | Red, semi-double flowers, lacking additional petaloids, smooth hose-in-hose flower appearance |
| Hybrid azalea 'Roblec' U.S. Plant Pat. No. 15,339 P2 | Light pink semi-double flowers, petaloids present; petals ruffled/petticoat like flowers. Flowers approximately |

TABLE 1-continued

| | |
|---|---|
| Hybrid azalea 'RLH1-2P8' U.S. Plant Pat. No. 21,477 P2 | Bright pink, semi-double flowers, petaloids present; petals ruffled/petticoat-like flowers |
| Hybrid azalea 'NCRX3' U.S. patent application Ser. No. 16/602,642 | Soft pink semi-double flowers, petaloids present; smooth rose-bud-like flowers. |
| Hybrid azalea 'NCRX4' | Bright lavender semi-double flowers; petaloids present; petals are ruffled and dense in the truss. |

| Plant | Habit | Additional characters |
|---|---|---|
| Hybrid azalea 'Roblez' U.S. Plant Pat. No. 28,279 P3 | Compact: 75 cm × 90 cm | Hardy to Zone 6 |
| Hybrid azalea 'Roblec' U.S. Plant Pat. No. 15,339 P2 | Mid-sized: 150 cm × 120 cm | Hardy to Zone 7 |
| Hybrid azalea 'RLH1-2P8' U.S. Plant Pat. No. 21,477 P2 | Mid-sized: 130 cm × 120 cm | Hardy to Zone 6 |
| Hybrid azalea 'NCRX3' U.S. patent application Ser. No. 16/602,642 | Compact: 50 cm × 90 cm | Hardy to Zone 6b |
| Hybrid azalea 'NCRX4' | Mid-sized: 100 × 100 cm | Hardy to Zone 6b |

BRIEF DESCRIPTION OF THE DRAWINGS

'NCRX4' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Rhododendron*.

DETAILED BOTANICAL DESCRIPTION

Figure 1:
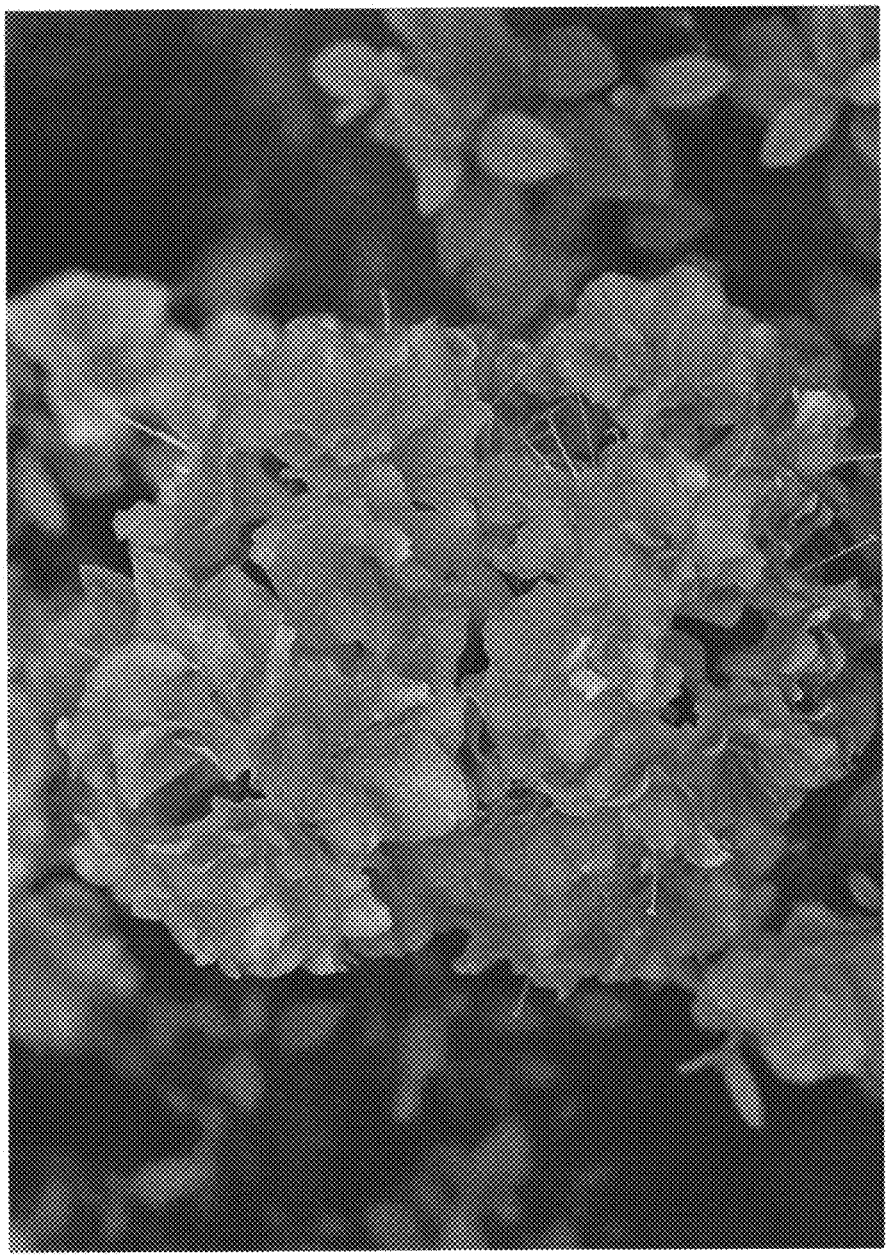
FIG. 1 shows fully expanded flowers as part of a full truss on a two-year-old container-grown plant in Grand Haven, Mich. in 2018.
Figure 2:
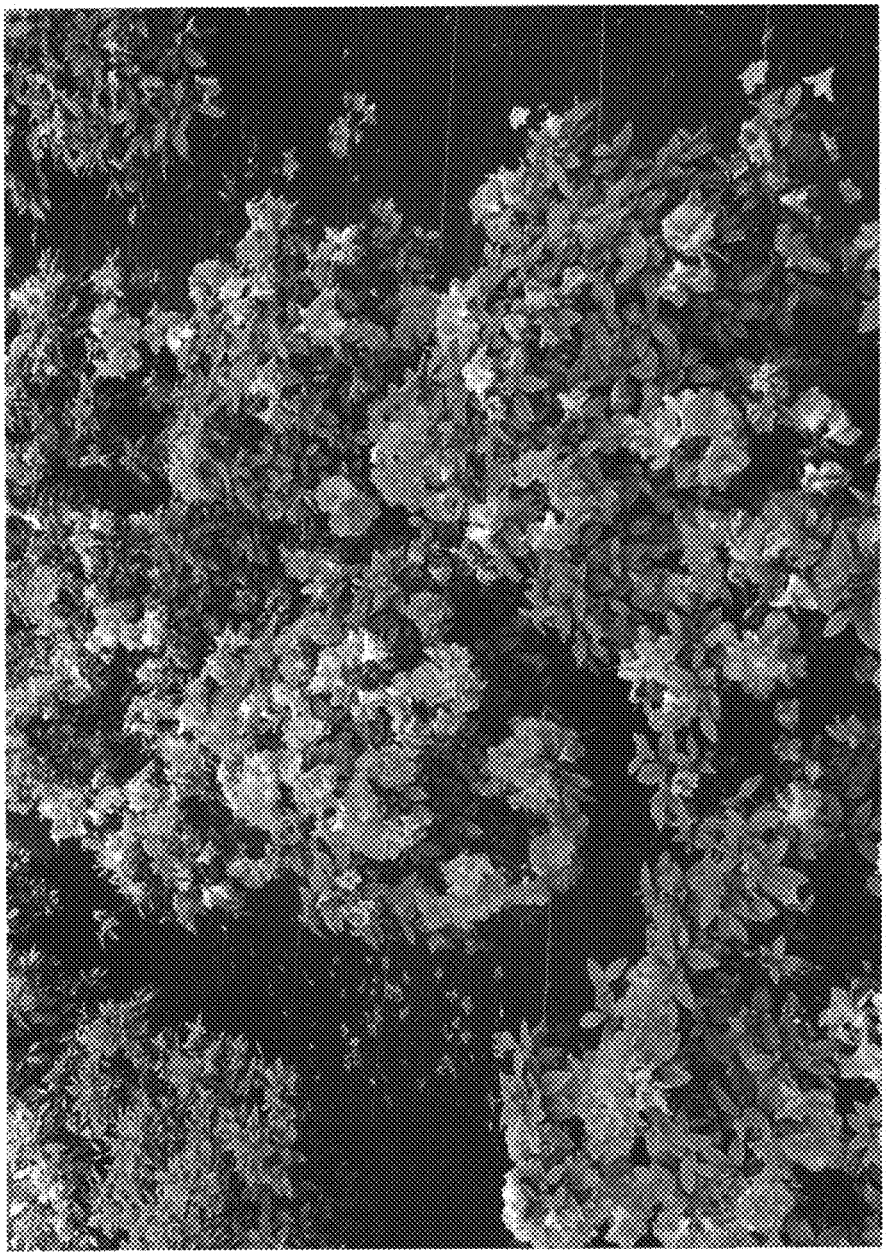
FIG. 2 shows the plant habit and form on 3-year-old container-grown plants in a greenhouse in Grand Haven, Mich. in 2018.
Figure 3:
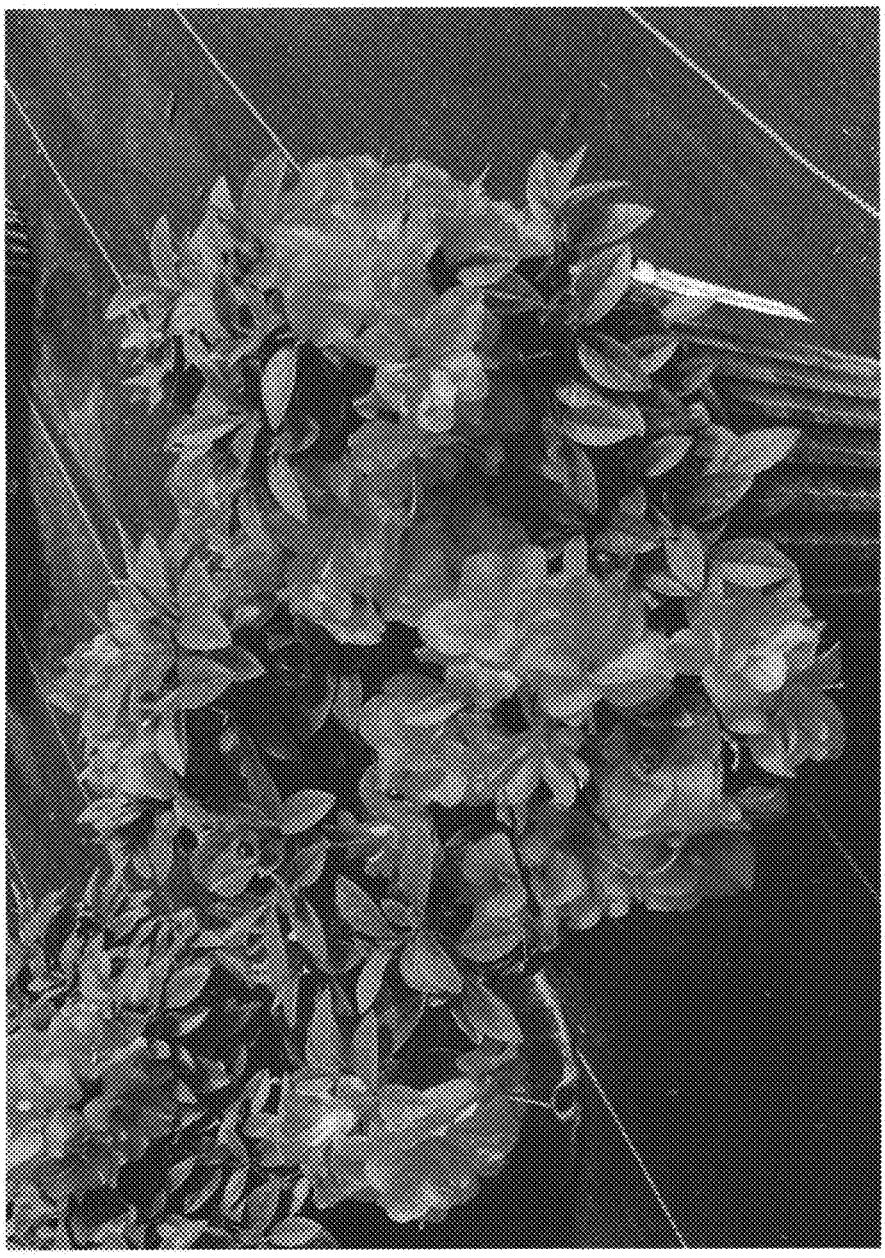
FIG. 3 shows individual flowers after anthesis the inflorescence with flower colors at different stages of development on a 2-year-old, container-grown plant in a greenhouse in Grand Haven, Mich. in 2018.

The following is a detailed description of the botanical characteristics of the new and distinct hybrid *Rhododendron* (azalea) known by the denomination 'NCRX4'. The detailed description was taken on a 3-year-old container-grown plant in Mills River, N.C. in 2019. Where pertinent, descriptive data was supplemented by observations/measurements taken on a 5 year-old individual located in field trials in Mills River, N.C. as well as information provided from cooperators in Grand Haven, Mich. Mills River trials were conducted in full sun in plastic-covered clay loam soils supplemented with mulch. All colors cited herein refer to The Royal Horticultural Society Colour Chart (The Royal Horticultural Society (R.H.S.), London, 2015 Edition). Where specific dimensions, sizes, colors, and other characteristics are described, it is to be understood that these descriptions are approximations for variable characters that are labile and may change as a result of environment and growing conditions.

PLANT

Plant type: Broad-leaf evergreen or semi-evergreen shrub.
Growth habit: Globose.
Height: 1 m.
Width: 1 m.
Growth rate: Moderate.
Roots: Fibrous.
Stems, shoots, branches, trunk:
Shoots/stems (softwood new growth):
- *Shape*.—Rounded.
- *Color*.—RHS Yellow-Green Group 146D, deepening in color towards the terminal end of the shoot to RHS Greyed-Purple Group 183C and 183D.
- *Texture*.—Pubescent.
- *Pubescence color*.—RHS Greyed-Orange Group N170.
- *Shoot diameter*.—Approximately 0.5-1.2 mm.
- *Shoot length*.—Variable, ranging from 1 cm up to 20 cm.

Stems (woody shoot):
- *Shape*.—Rounded.
- *Color*.—Mix of RHS Grey-Brown Group 199A, 199B and N199A N199B occasionally with RHS Greyed-Orange Group 175A streaks.
- *Texture*.—Pubescent.
- *Pubescence color*.—RHS Greyed-Orange Group mix of 174A and 174B.
- *Stem diameter*.—Generally 2.0 to 3.5 mm.
- *Stem length*.—Variable, ranging from 5 to 20 cm.
- *Stem aspect*.—0-90°.

Branches (mature growth having at least two woody stems):
- *Shape*.—Rounded.
- *Color*.—Mix of RHS Brown Group 200B, 200C and RHS Grey-Brown Group N199B.
- *Texture*.—Gently exfoliating.
- *Branch diameter*.—Variable, ranging from 4-11 mm.
- *Branch length*.—Variable, ranging from 20-40 cm.
- *Branching*.—Freely branched.

Number of lateral branches: Approximately 7-25.

FOLIAGE

*Type*.—Evergreen to semi-evergreen.
*Arrangement*.—Alternate.
*Division*.—Simple.
*Shape*.—Obelliptic.
*Apex*.—Mucronate.
*Base*.—Cuneate.
*Margin*.—Entire, cilliate.
*Venation*.—Reticulate.
*Internode length*.—Approximately 2-10 mm.
*Leaf color*.—
*Immature leaf*.—Adaxial (upper) surface: Color: RHS Yellow-Green Group 144A, sometimes mixed with RHS Green Group 143A in the sun. Surface: Pubescent. Pubescence color: RHS Green-White Group 157B, 157C. Abaxial (lower) surface: Color: RHS Yellow-Green Group N144D. Surface: Pubescent. Pubescence: RHS Green-White Group 157B, 157C.
*Mature leaf*.—Length: Approximately 1.5-3 cm. Width: Approximately 1-2 cm. Color: Adaxial (upper) surface: RHS Yellow-Green Group 146A, 146B. Abaxial (lower) surface: RHS Yellow-Green Group 146B, 146C. Surface: Both sides are lightly pubescent.

*Leaf attachment*.—Petiolate.

*Petiole*.—Shape: Lunate. Length: Approximately 6-8 mm. Diameter: Approximately 1-1.5 mm. Color: Adaxial side: RHS Yellow-Green Group 144C mixed with N144D. Abaxial side: RHS Yellow-Green Group 144C mixed with N144D. Texture: Both sides are pubescent. Pubescence color: RHS Greyed-Orange Group N170B.

Fall/winter color:

*Adaxial side*.—Mix of RHS Greyed-Purple Group N186A N186B and RHS Brown Group 200A, 200B.

*Abaxial side*.—Mix of RHS Yellow-Green Group 146B, 146C and 147B, 147C. In some instances browning was observed as RHS Greyed-Orange Group 177A, 177B.

FLOWER

Inflorescence:

Type: Congested terminal raceme (truss).

Flowering season: Mid-Spring (Mid-April-Early May) reblooms in Early Fall (Late September to early October) In Michigan and North Carolina.

Flowering habit: Free-flowering.

Flower number: 3-7 flowers per truss.

Consistency in display: Blooms reliably in the spring and consistently reblooms in the fall.

Lastingness of flowers: Each flower lasts approximately 5-8 days.

Fragrance: None.

Self-cleaning or persistent: Persistent.

Truss bud:

Length: 5-10 mm.

Diameter: 5-10 mm.

Bud scales:

*Number*.—Variable: 3-7.

*Length*.—Approximately 10-12 mm.

*Width*.—Approximately 9-12 mm.

*Color prior opening*.—RHS Yellow-Green Group 145B with pubescent stripe along the center that runs from the base of the bud scale to its tip in RHS Greyed-Orange Group 164A.

*Color after flowers emerge*.—Bud scales fade to RHS Yellow-White Group 158A.

Emerging floral buds:

Shape: Elliptic, acuminate.

Length: 1.5-3.5 cm.

Diameter: 5-10 mm.

Color: RHS Red-Purple Group 70B, lightening to 69A along the petal mid-rib.

Perianth:

Diameter at anthesis: 7-9 cm.

Depth: 3-4 cm.

Organization: Petals are arranged in two whorls.

Aspect: Facing upwards and outwards.

Shape: Broadly funnel-shaped.

Attachment: Pedicellate.

Petals: Generally, petals in the first and second whorls have similar dimensions and shapes. Occasionally flowers include anther-derived petaloids, but the occurrence is generally rare.

Length: 4-5 cm.

Width: 2-3 cm.

Shape: Obovate.

Apex: Obtuse.

Base: Acuminate.

Margin: Undulate (ruffled).

Fused or unfused: Fused at the midpoint.

Color:

*While opening*.—

*Adaxial (upper) surface*.—At the base, petals are generally RHS Red-Purple Group 73D, and intensify in color to RHS Red-Purple Group N74B.

*Blotch*.—RHS Red-Purple Group 60A. Blotch is generally present on 3 petals in each whorl.

*Surface*.—Smooth, silky.

*Abaxial (lower) surface*.—At the base, the petals exhibit coloration in RHS Green-White Group 157B, and intensify in color to RHS Red-Purple group 69C. The petal midrib is lighter in coloration, fading from RHS Red-Purple 69A, to 69C, 69D and eventually RHS White Group 155C giving the impression that the midvein of the petal forms a stripe.

*Surface*.—Slightly pubescent.

*Open/anthesis*.—

*Adaxial (upper) surface*.—The base of the petal exhibits coloration in RHS Red-Purple Group 69D strengthening in color to RHS Red-Purple Group 71D.

*Blotch*.—RHS Red-Purple Group 60B.

*Surface*.—Smooth, silky.

*Abaxial (lower) surface*.—The base of the petal is RHS Red-Purple Group 69D increasing in color to RHS Red-Purple Group 72C. Coloration fades in intensity towards the midrib of the petal to RHS Red-Purple Group 73D.

*Surface*.—Smooth, silky.

*Open/post-anthesis*.—

*Adaxial (upper) surface*.—

*Base*.—RHS White Group N155D.

*Midpoint*.—RHS Purple Group NN78D.

*Tip*.—RHS Purple Group NN78D.

*Blotch*.—RHS Purple Group NN78D.

*Surface*.—Slightly pubescent.

*Abaxial (lower) surface*.—

*Base*.—RHS White Group N155D.

*Midpoint*.—RHS Red-Purple Group 70C.

*Tip*.—RHS Red-Purple Group 70C.

*Surface*.—Smooth, silky.

Calyx/receptacle:

Shape: Star-shaped, single-whorl of persistent sepals.

Sepals:

*Number*.—5.

*Length*.—6-9 mm.

*Width*.—4-6 mm.

*Shape*.—Lanceolate.

*Apex*.—Acuminate.

*Margin*.—Entire, cilliated.

*Fused or unfused*.—Fused at base.

*Color*.—RHS Yellow-Green Group 145A.

*Surface*.—Adaxial side is glabrous; abaxial side is pubescent.

Pedicels:

*Shape*.—Rounded.

*Length*.—10-20 mm.

*Diameter*.—1-2 mm.

*Color.*—RHS Yellow Green Group 144C; some blushing on the adaxial sides, particularly in the sun in RHS Orange-Red Group N34B.

*Surface.*—Pubescent.

REPRODUCTIVE ORGANS

Most likely as an effect of petal doubling, reproductive characters, especially style length, stigmatic surface dimensions, stamen number, and anther dimensions can be highly variable. Some flowers exhibit stunted styles, filaments, and/or anthers. Generally, flowers are both complete and perfect, although individual flowers may vary.

Gynoecium:
Pistil number: 0-1.
Pistil length: 2-5 mm.
Pistil diameter: Approximately 0.5 mm.
Stigma shape: Orbicular to elliptic.
Stigma length: 1-2 mm.
Stigma width: 1-2 mm.
Stigma color: RHS Yellow-Green Group N144C when opening, mixed with RHS Red-Purple Group 58C when receptive.
Style color: RHS Yellow-Orange Group when opening; RHS Red-Purple Group 58C when receptive.
Ovary shape: Dome-shaped.
Ovary length: 4-5 mm.
Ovary diameter: 1-2 mm.
Ovary color: RHS Green Group 143C.
Surface: Pubescent.
Androecium:
Stamen number: 0-7.
Anther shape: Ovoid with two apical pores.
Anther attachment: Dorsifixed.
Anther length: 2-4 mm.
Anther width: Approximately 1 mm.
Anther color: RHS Greyed-Orange Group 177D.
Filament length: 15-35 mm.
Filament diameter: Approximately 0.5 mm.
Filament color: RHS White Group 155A.
Amount of pollen: Moderate.
Pollen type: Vicinate.
Pollen color: RHS White Group NN155C.

OTHER CHARACTERISTICS

Fruit type: Capsule.
Fruit texture: Pubescent.
Fruit length: Approximately 10 mm if successfully pollinated, 5 mm if not.
Fruit diameter: Approximately 5 mm if successfully pollinated, 2.5 mm if not.
Fruit color:
Immature: RHS Yellow-Green Group 152B.
Mature: RHS Grey-Brown Group N199C.
Seed number: Variable 0 to over 100.
Seed length: Approximately 1 mm.
Seed diameter: Approximately 0.5 mm.
Seed color: RHS Yellow-Orange Group 22A.
Propagation: Roots readily (>90%) from firm, terminal, softwood stem cuttings taken in mid-summer. 'NCRX4' roots well when the bottom 2 cm of the stems are treated for 5 seconds with 3,000 ppm of potasium salt of indole butyric acid (KIBA) dissolved in water and placed under intermittent mist for 8-10 weeks until roots form.
Disease and insect resistance: No significant disease or insect pests have been observed.
Cold hardiness: Has been reliably cold hardy in USDA 6b.

What is claimed is:

1. A new and distinct cultivar of *Rhododendron* plant named 'NCRX4' as herein illustrated and described.

* * * * *